United States Patent [19]

Christidis et al.

[11] Patent Number: 4,483,868
[45] Date of Patent: Nov. 20, 1984

[54] GASTRO-PROTECTING ACTIVITY

[75] Inventors: Yani Christidis; Robert Fournex, both of Paris; Colette Tournemine, Livry-Gargan, all of France

[73] Assignee: Roussel Uclaf, Romainville, France

[21] Appl. No.: 256,932

[22] Filed: Apr. 23, 1981

[30] Foreign Application Priority Data

Apr. 24, 1980 [FR] France ............................ 80 09216

[51] Int. Cl.³ .................. A61K 31/36; A61K 31/235; A61K 31/24; A61K 31/19
[52] U.S. Cl. .................................. 424/282; 424/308; 424/309; 424/317; 549/436; 560/51; 562/459
[58] Field of Search .................. 424/282, 308, 317; 549/436; 560/51; 562/459

[56] References Cited

U.S. PATENT DOCUMENTS

| | | |
|---|---|---|
| 2,532,579 | 12/1950 | Thomas . |
| 2,562,208 | 7/1951 | Papa et al. . |
| 3,753,997 | 8/1973 | Ash et al. . |
| 3,763,148 | 10/1973 | Ash et al. . |
| 3,846,470 | 11/1974 | Raube et al. . |
| 3,910,959 | 10/1975 | Vallet ................................ 424/282 |
| 3,940,404 | 2/1976 | Ash et al. . |
| 3,940,487 | 2/1976 | La Croix et al. .................. 424/282 |
| 3,953,463 | 4/1976 | Ash et al. . |
| 4,017,517 | 4/1977 | Murata et al. ..................... 549/436 |
| 4,334,089 | 6/1982 | Kraas et al. ........................ 424/317 |
| 4,402,978 | 9/1983 | Christidis et al. .................. 424/282 |

FOREIGN PATENT DOCUMENTS

| | | |
|---|---|---|
| 1282644 | 11/1968 | Fed. Rep. of Germany ........ 560/51 |
| 2047806 | 4/1972 | Fed. Rep. of Germany ...... 562/459 |
| 2103749 | 8/1972 | Fed. Rep. of Germany . |
| 2501834 | 7/1975 | Fed. Rep. of Germany . |
| 1566213 | 3/1969 | France . |
| 1566212 | 6/1973 | France . |
| 8495M | 7/1973 | France . |
| 2132354 | 4/1975 | France . |
| 2270856 | 12/1975 | France . |
| 55-36434 | 3/1980 | Japan ................................ 562/459 |
| 591415 | 9/1977 | Switzerland . |
| 588108 | 6/1947 | United Kingdom . |
| 1387733 | 3/1975 | United Kingdom . |

OTHER PUBLICATIONS

*Journal of American Pharmaceutical Association*, vol. 37, No. 11, Nov. 1948, pp. 439–449.
*Chemical Abstracts*, vol. 88, No. 5, Jan. 30, 1978, Abstract 37442p.

*Journal of the American Chemical Society*, vol. 71, No. 4, Apr. 1949, F. K. Kirchner et al., pp. 1210–1213.
*Journal of the American Chemical Society*, vol. 70, No. 10, Oct. 1948, D. Papa et al., pp. 3356–3360.
*European Journal of Medical Chemistry Chimica Therapeutica*, vol. 12, Jan.–Feb. 1977, pp. 17–20.
*European Journal of Medical Chemistry Chimica Therapeutica*, vol. 13, No. 3, May–Jun. 1978, H. Orzalesi et al., pp. 259–264.
*Journal of Pharmaceutical Sciences*, vol. 66, No. 4, Apr. 1977, pp. 466–476, Child, Ralph G., et al., "Fenbufen, a New Anti-Inflammatory Analgesic: Synthesis and Structure—Activity Relationships of Analogs".
*Journal of Medicinal Chemistry*, vol. 15, No. 9, Sept., 1972, pp. 918–922, Markovac, A., et al.,–"Antimalarials, 3, 2,6–Bis(aryl)–4–pyridinemethanols with Trifluoromethyl Substituents".
*Journal of Organic Chemistry*, vol. 35, No. 5, May 1970, pp. 1367–1376, Petit, George R., et al., "Bufadienolides, 1., Introduction and Base-Catalyzed Condensation of Methyl Ketonds with Glyoxylic Acid".
*J.A.C.S.*, vol. 46, No. 10, Oct. 1924, pp. 2319–2326 RICE, Grace Potter, "The Isomeric Esters of Para-Ethoxy-Benzoylacrylic Acid".

*Primary Examiner*—Ethel G. Love
*Attorney, Agent, or Firm*—Stevens, Davis, Miller & Mosher

[57] ABSTRACT

Diseases and ailments accompanied by gastric and gastroduodenal lesions treated by administering a compound of the formula (I)

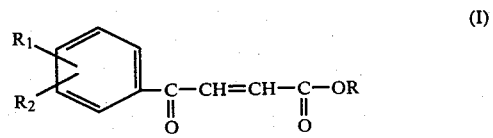

in which R represents hydrogen or alkyl containing 1 to 5 carbon atoms and $R_1$ and $R_2$, identical or different, both represent alkoxy containing 1 to 3 carbon atoms, or both represent halogen, or $R_1$ represents hydrogen and $R_2$ represents halogen, nitro or trifluoromethyl, or $R_1$ and $R_2$ form a methylenedioxy group at adjacent carbon atoms, as well as pharmaceutically acceptable salts thereof, particularly alkali metal, alkaline earth metal, or amine salts of said acid.

20 Claims, No Drawings

GASTRO-PROTECTING ACTIVITY

The present invention relates to the treatment of diseases and ailments accompanied by gastric and gastroduodenal lesions by administering certain substituted derivatives of 4-phenyl-4-oxo-2-butenoic acid which exhibit gastric acid secretion inhibiting and cytoprotecting activity, and to pharmaceutical compositions containing those compounds.

More particularly, the present invention relates to inhibiting gastric acid secretion and gastric cytoprotection with compounds represented by the formula (I)

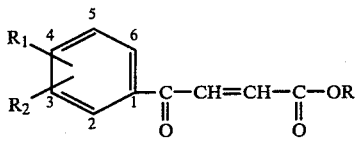

in which R represents hydrogen or alkyl containing 1 to 5 carbon atoms and $R_1$ and $R_2$, identical or different, both represent alkoxy containing 1 to 3 carbon atoms, or both represent halogen, or $R_1$ represents hydrogen and $R_2$ represents halogen, nitro or trifluoromethyl, or $R_1$ and $R_2$, attached to adjacent carbon atoms, form a methylenedioxy group, as well as pharmaceutically acceptable salts thereof, particularly alkali metal, alkaline earth metal, or amine salts of said acid.

Some of these compounds are known in the prior art. See, for example, U.S. Pat. Nos. 2,532,579 and 2,562,208, as well as British Pat. No. 588,108 and French Pat. No. 2,270,856. However, the gastroprotecting activity of such compounds has not heretofore been reported. Moreover, the compounds of formula (I), wherein $R_1$ and $R_2$ form a methylenedioxy group located on carbon atoms 2–3 are belevied to be novel.

Preferred compounds of formula (I) are those wherein R is as defined above, $R_1$ and $R_2$, identical or different, both represent alkoxy containing 1 to 3 carbon atoms, or both represent halogen, or $R_1$ represents hydrogen and $R_2$ represents halogen, nitro group, or trifluoromethyl, as well as the pharmaceutically acceptable alkali metal, alkaline earth metal, or amines salts of said compounds in which R represents hydrogen.

The term "alkyl containing 1 to 5 carbon atoms", includes, for example, methyl, ethyl, n-propyl, isopropyl, n-butyl, isobutyl, tert.-butyl and pentyl.

The term "alkoxy containing 1 to 3 carbon atoms" includes, for example, methoxy, ethoxy, n-propoxy and isopropoxy.

The term "halogen atom" includes, for example, chlorine, bromine and fluorine.

The alkali metal or alkaline earth metal salts of compounds of formula (I) in which R represents a hydrogen atom include, for example, sodium salts, potassium salts, lithium salts and calcium salts.

The amine salts of compounds of formula (I), in which R represents a hydrogen atom, are the usual amine salts. Among the usual amines, there can be mentioned the monoalkylamines, such as, for example, methylamine, ethylamine, propylamine; the dialkylamines, such as, for example, dimethylamine, diethylamine, di-n-propylamine; and, trialkylamines, such as, triethylamine. There can likewise be mentioned piperidine, morpholine, piperazine and pyrrolidine.

Referred compounds of formula (I) are those wherein $R_1$ and $R_2$ identical or different, both represent alkoxy containing 1 to 3 carbon atoms, or both represent halogen, or $R_1$ represents hydrogen and $R_2$ represents fluoro, 2-nitro or trifluoromethyl or $R_1$ and $R_2$ located on adjacent carbon atoms, form a methylene dioxy group.

More preferred compounds of formula (I) are those wherein $R_1$ and $R_2$, identical or different, both represent alkoxy containing 1 to 3 carbon atoms, or both represent halogen, or $R_1$ represents hydrogen and $R_2$ represents trifluoromethyl or fluorine, particularly trifluoromethyl, as well as the pharmaceutically acceptable alkali metal, alkaline earth metal, or amine salts of the said formula (I) in which R represents hydrogen.

Of the products of formula (I) above in which $R_1$ and $R_2$ both represent alkoxy containing 1 to 3 carbon atoms, in particular the products of formula (I) above in which $R_1$ and $R_2$ each represent methoxy, there is mentioned in particular (E) 4-(3,4-dimethoxyphenyl)-4-oxo-2-butenoic acid and (E) 4-(2,5-dimethoxyphenyl)-4-oxo-2-butenoic acid, as well as their pharmaceutically acceptable alkali metal, alkaline earth metal, and amine salts.

Of the products of formula (I) above, in which $R_1$ and $R_2$ both represent halogen, there is mentioned in particular (E) 4-(3,4-dichlorophenyl)-4-oxo-2-butenoic acid, and its pharmaceutically acceptable alkali metal, alkaline earth metal, and amine salts.

Of the products of formula (I) above in which $R_1$ represents hydrogen and $R_2$ represents trifluoromethyl, there is mentioned in particular (E) 4-(4-trifluoromethylphenyl)-4-oxo-2-butenoic acid and its pharmaceutically acceptable alkali metal, alkaline earth metal, and amine salts.

Of the products of formula (I) above in which $R_1$ and $R_2$, located on adjacent carbon atoms, together form methylenedioxy, there is mentioned particularly (E) 4-(3,4-methylenedioxyphenyl)-4-oxo-2-butenoic acid and its pharmaceutically acceptable alkali metal, alkaline earth metal, and amine salts.

Of the products of formula (I) above in which $R_1$ represents hydrogen and $R_2$ represents halogen, there is mentioned particularly (E) 4-(4-fluorophenyl)-4-oxo-2-butenoic acid and its pharmaceutically acceptable alkali metal, alkaline earth metal, and amine salts.

The products of formula (I) can exist in the form of cis or trans geometrical isomers, and these different isomers, of course, come within the scope of the invention.

The products defined above constitute, according to the invention, medicaments which are very useful in human therapy, particularly for the treatment of hyperchlorhydria, gastric ulcers, gastroduodenal ulcers, gastritis, hiatal hernia and gastroduodenal diseases accompaniedly gastric hyperacidity.

The dosage, which is variable according to the product utilized and the disease in question, can range, for example, between 0.05 g and 2 g, preferably between 0,2 g and 1,5 g per day in the adult by oral administration.

A further object of the present invention is to provide pharmaceutical compositions which contain as the active principle at least one of the above-mentioned compounds. These compositions are prepared so as to be administrable via the digestive path or parenterally.

They can be solid or liquid and exist in the pharmaceutical forms currently utilized in human medicine, such as, for example, plain or coated tablets, capsules, granules, suppositories, and injectable preparations; they are prepared by the usual methods.

The active principle or principles can be incorporated in excipients usually used in these pharmaceutical compositions, such as, talc, gum arabic, lactose, starch, magnesium stearate, cocoa butter, aqueous or non-aqueous vehicles, fatty bodies of animal or vegetable origin, paraffinic derivatives, glycols, various wetting agents, dispersants or emulsifiers, and preservatives.

The products of formula (I) can be prepared by methods known in the art. They can be prepared, for example, by condensation of glyoxylic acid with an acetophenone substituted on the phenyl group in the presence of acetic anhydride at about 130° C., according to a process described in Japanese Patent Application No. 77-39020, published on Oct. 2, 1977 (C.A. 88: 37442p), or in J. Med. Chem., 1972, Vol. 15, No. 9, 918–22.

As stated in J. Med. Chem., 1972, Vol. 15, No. 9, 918–22, the operation can likewise be performed in two stages, by preparing a phenyl-4-oxo-4-hydroxy-2-butanoic acid substituted on the phenyl nucleus by condensation of glyoxylic acid with an acetophenone substituted on the phenyl nucleus at about 80° C., and dehydration of the product obtained. Products of formula (I) have been prepared in this way, the condensation being carried out at about 95° C. and by dehydrating the product obtained with a hot acid. Examples of such preparations are further described below.

The products of formula (I) in the form of cis isomers which are not already known can be prepared from the corresponding trans isomers by irradiation as disclosed in J. Org. Chem., 13, 1948, pp. 284–296.

The alkali metal, alkaline earth metal, or amine salts of products of formula (I) can be prepared, whey they are not already known, in the usual manner, by reaction of the corresponding bases with the said products of formula (I).

The reaction is preferably carried out in a solvent or a solvent mixture, such as water, ethyl ether, ethanol, acetone or ethyl acetate.

The products of formula (I) in which R represents an alkyl group containing 1 to 5 carbon atoms which are not already known can be prepared in the usual manner, by the action on the corresponding acid of formula (I) of an alcohol of formula ROH, preferably in an acid medium. The acid can be, for example, hydrochloric acid or phosphoric acid.

The examples presented below are for the purpose of illustrating the invention without, however, limiting it to these specific embodiments.

EXAMPLE 1

(E) 4-(3,4-dimethoxyphenyl)-4-oxo-2-butenoic acid

Method A.

14.8 g of glyoxylic acid, 50% by weight in water, are heated under reduced pressure to eliminate the greater part of the water present (80%); there are then introduced into the reaction medium 36 g of 3,4-dimethoxy-acetophenone and 40 cm$^3$ of acetic acid.

This solution is then heated under reflux for 20 hours. The reaction medium is cooled to room temperature, crystallization is initiated, and the suspension obtained is kept for one hour at 15° C. The precipitate formed is then filtered, washed by pasting with 10 cm$^3$ of acetic acid, then dried under vacuum at 80° C. There are thus isolated 11.2 g of 4-(3,4-dimethoxyphenyl)-4-oxo-2-butenoic acid. m.p.=181°±1° C.

The filtrate, after 10 cm$^3$ of acetic acid has been distilled off under reduced pressure is re-utilized in a second operation with 14.8 g of glyoxylic acid, 50 wt.% in water, previously concentrated under vacuum to about 80-83%, and 18 g of 3,4-dimethoxy-acetophenone. After the same treatments, there are isolated 21.6 g of the expected acid; m.p.=181° C.

Elemental Analysis ($C_{12}H_{12}O_5$—236.20)

|  | C % | H % |
| --- | --- | --- |
| Calculated | 61.01 | 5.12 |
| Found | 61.1 | 5.2 |

Physical Analyses

NMR Spectrum—in solution in $D_6$ acetone in presence of $D_6$ dimethylsulfoxide: δ=3.82 ppm, 2s separated by 1 Hz, 6H, —OCH$_3$; δ=6.66 ppm, d, J=16 Hz, 1H, —CH=CH—; δ=7.8 ppm, d, J=16 Hz, 1H, —CH=CH—; δ=6.8 ppm, d, 1H, JH$_5$H$_6$=8 Hz, aromatic; δ=7.42 ppm, d, 1H, JH$_2$H$_6$=1 Hz, aromatic; δ=7.6 ppm, q, 1H, JH$_6$H$_5$=8 Hz, aromatic, JH$_6$H$_2$=1 Hz.

Acidimetry: 100% of theoretical.

Method B.

Stage 1:
4-(3,4-dimethoxyphenyl)-4-oxo-2-hydroxybutanoic acid 52 g of glyoxylic acid, 50 wt.% aqueous solution, are heated under reduced pressure so as to distill off the major part (80%) of the water present, then after cooling to ambient temperature there are added 126 g of 3,4-dimethoxy-acetophenone. Heating then proceeds for 3 hours under vacuum at 95° C.

After the reaction medium has been cooled to ambient temperature, 250 cm$^3$ of water containing 20.3 g of sodium carbonate and 50 cm$^3$ of ethyl ether are added.

After decantation, the aqueous phase is washed with ether, then the organic phases with water. The combined aqueous phases are then acidified to pH 1 with hydrochloric acid (50%), then extracted with ethyl acetate.

There are thus obtained 91 g of the expected acid in crystallized form.

Stage 2: (E) 4-(3,4-dimethoxyphenyl)-4-oxo-2-butenoic acid

The acid obtained in the preceding stage is heated for 150 minutes under reflux in 100 cm$^3$ acetic acid and 10 cm$^3$ of concentrated hydrochloric acid, d=1.18.

The suspension obtained is then cooled to ambient temperature, then, after being kept for several hours, the crystalline precipitate formed is filtered, washed with several cm$^3$ of acetic acid, and then dried under reduced pressure at 80° C. There are thus obtained 55 g of (E) 4-(3,4-dimethoxyphenyl)-4-oxo-2-butenoic acid. m.p.=181±1° C.

Elemental Analysis ($C_{12}H_{12}O_5$=236.20)

|  | C % | H % |
| --- | --- | --- |
| Calculated | 61.01 | 5.12 |
| Found | 61.1 | 5.2 |

This acid, treated with methanol under reflux in the presence of paratoluenesulfonic acid monohydrate, gives (E) methyl 4-(3,4-dimethoxyphenyl)-4-oxo-2-butenoate, with a yield of 80%. m.p.=92±1° C.

Elemental Analysis ($C_{13}H_{14}O_5 = 250.25$)

|  | C % | H % |
|---|---|---|
| Calculated | 62.39 | 5.64 |
| Found | 62.4 | 5.7 |

EXAMPLES 2-6

Operating according to Method B of Example 1, the following products were prepared:
(E) 4-(4-chlorophenyl)-4-oxo-2-butenoic acid
(E) 4-(4-fluorophenyl)-4-oxo-2-butenoic acid
(E) 4-(3,4-dichlorophenyl)-4-oxo-2-butenoic acid
(E) 4-(2-nitrophenyl)-4-oxo-2-butenoic acid
(E) 4-(4-trifluoromethylphenyl)-4-oxo-2-butenoic acid
(see Table 1).

TABLE 1

| | First stage - (intermediate product) | | Second stage - (final product) | |
|---|---|---|---|---|
| Example No. | Product | m.p. | Product | m.p. |
| 2 | 4-(4-chlorophenyl)-4-oxo-2-hydroxy-butanoic acid | 137° C., a | (E)* 4-(4-chlorophenyl)-4-oxo-2-butenoic acid | 159° C., b |
| 3 | 4-(4-fluorophenyl)-4-oxo-2-hydroxy-butanoic acid | 127° C., a | (E) 4-(4-fluorophenyl)-4-oxo-2-butenoic acid | 134° C., a |
| 4 | 4-(3,4-dichlorophenyl)-4-oxo-2-hydroxy-butanoic acid | 146° C., b | (E) 4-(3,4-dichlorophenyl)-4-oxo-2-butenoic acid | 143° C., a |
| 5 | 4-(2-nitrophenyl)-4-oxo-2-hydroxy-butanoic acid | 108° C., a | (E) 4-(2-nitrophenyl)-4-oxo-2-butenoic acid | 170° C., b |
| 6 | 4-(4-trifluoromethylphenyl)-4-oxo-2-hydroxy-butanoic acid | 119° C., a | (E) 4-(4-trifluorophenyl)-4-oxo-2-butenoic acid | 155° C., b |

Crystallization solvents =
a 1,2-dichloroethane
b ethyl acetate

EXAMPLE 7

(E) 4-(2,5-dimethoxyphenyl)-4-oxo-2-bentenoic acid

Stage A:
4-(2,5-dimethoxyphenyl)-4-oxo-2-hydroxy-butanoic acid 22.2 g of glyoxylic acid, 50 wt.% in water, are heated under reduced pressure until about 80% of the water present has been eliminated; then, after cooling, 54 g of 2,5-dimethoxyacetophenone are added, i.e., an excess of 100% over theoretical.

While heating at 95° C. for 150 minutes under reduced pressure, the residual water is simultaneously distilled off. There are then introduced, after cooling the medium to ambient temperature 60 cm³ of ether and 100 cm³ of distilled water containing 8.7 g of pure, dry sodium carbonate.

After decantation, the organic ether phase is washed, then the united aqueous phases are acidified to pH 1 with 6N hydrochloric acid. The desired product is then extracted with ethyl acetate. After washing, drying and elimination under vacuum of the extraction solvent, the desired product is isolated in the form of an oil, which crystallizes spontaneously on cooling.

After recrystallization from 1,2-dichloroethane, there is obtained the expected 4-(2,5-dimethoxyphenyl)-4-oxo-2-hydroxy-butanoic acid. m.p.=89° C.

Stage B: (E) 4-(2,5-dimethoxyphenyl)-4oxo-2-butenoic acid

There is heated under reflux a mixture containing 13 g of the acid obtained in Stage A, 15 cm³ of acetic acid, and 1.5 cm³ of concentrated hydrochloric acid.

The solution obtained is then cooled to ambient temperature, then, after keeping for several hours, the crystallized precipitate formed is filtered off. There are thus obtained 8.8 g of crude product (m.p.=150° C.). After recrystallization from 50 cm³ of ethyl acetate, there are obtained 7 g of the expected product. m.p.=151° C.

Analysis ($C_{12}H_{12}O_5 = 236.2$)

|  | C % | H % |
|---|---|---|
| Calculated | 61.01 | 5.12 |
| Found | 61.2 | 5.3 |

EXAMPLE 8

(E) 4-(3,4-methylenedioxyphenyl)-4-oxo-2-butenoic acid 44 g of glyoxylic acid, 50 wt.% in water, are heated under reduced pressure to eliminate the major part (80%) of the water present; there are then introduced into the reaction medium 49.2 g of 3',4'-methylenedioxy-acetophenone, and 100 cm³ of acetic acid.

This solution is then heated for 20 hours under reflux, then the reaction medium is introduced and the product formed crystallizes. After filtration and washing with acetic acid, there are obtained 20.3 g of crude product which, after recrystallization from acetic acid, give 18.1 g of the expected product. m.p.=207° C.

Analysis ($C_{11}H_8O_6 = 220.2$)

|  | C % | H % |
|---|---|---|
| Calculated | 60.00 | 3.66 |
| Found | 60.3 | 3.7 |

PHARMACEUTICAL FORMS

EXAMPLE 9

Tablets

Tablets were prepared corresponding to the following formulation:
(E) 4-(3,4-dimethoxyphenyl)-4-oxo-2-butenoic acid: 100 mg
Excipient q.s. for a final tablet to: 300 mg
(details of excipient: lactose, wheat startch, treated starch, rice starch, magnesium stearate, talc).

EXAMPLE 10

Capsules

Capsules were prepared corresponding to the following formulation:
(E) 4-(4-fluorophenyl)-4-oxo-2-butenoic acid: 100 mg
Excipient q.s. for a final capsule of: 300 mg
(details of excipient: talc, magnesium stearate, aerosil).

PHARMACOLOGICAL STUDY (1) Determination of Anti-Ulcer Activity

The method used is described by SHAY et al. in Gastroenterology, 5, 43 (1945).

The Shay method consists of inducing ulcers in rats at the stomach level by ligature of the pylorus.

The animals are anesthetized with ether. A longitudinal incision is made about 1 cm below the sternum, the glandular part of the stomach and the duodenum are exposed, and a ligature is placed several mm below the pylorus. The muscular sheet is left as it is, and the skin is sutured with two clips.

As soon as possible afterwards, the animals receive the dispersive or the substance to be studied via the mouth in a volume of 0.5 ml/100 g and are kept without food or drink until sacrificed by carotid bleeding, which takes place about 16 hours after the treatment.

Before removing the stomach, a ligature is placed above the cardia.

The gastric liquid is collected in order to measure the pH.

The stomach is then opened along the major curvature, rinsed with physiological serum, and spread out on millimeter paper to be examined under a binocular magnifier.

The severity of the lesions is evaluated macroscopically and graded from 0 to 4 for each stomach.

The mean intensity of ulcerations is determined for each group of rats, and the protection is calculated by taking the ratio of the mean index of the treated group to the mean index of the control group.

The value of the gastric pH for the treated and control animals are likewise determined.

The following results reported in Table 2 were obtained.

TABLE 2

| Product of Example | Dose (mg/kg) | pH of gastric liquid treated animals | pH of gastric liquid control animals | Ulcerations % of protection with respect to controls |
|---|---|---|---|---|
| 1 | 20 | 4.3 | 2.2 | 100% |
|   | 4 | 2.6 | 1.7 | 83% |
|   | 0.8 | 2.9 | 2.2 | 0% |
| 2 | 25 | 5.6 | 2.0 | 100% |
|   | 5 | 3.0 | 1.8 | 57% |
|   | 1 | 3.0 | 2.6 | 0% |
| 3 | 10 | 4.0 | 2.5 | 100% |
|   | 2 | 2.8 | 2.7 | 43% |
|   | 0.4 | 3.1 | 2.6 | 20% |
| 4 | 20 | 4.1 | 2.7 | 71% |
|   | 4 | 3.1 | 2.7 | 14% |
| 5 | 20 | 4.3 | 2.5 | 100% |
|   | 4 | 3.3 | 2.6 | 19% |
| 6 | 100 | 6.3 | 2.6 | 98% |
|   | 20 | 2.8 | 1.8 | 67% |
|   | 4 | 2.3 | 1.2 | 55% |
|   | 0.8 | 1.4 | 2.3 | 20% |
| 7 | 50 | 4.2 | 1.6 | 100% |
|   | 10 | 3.0 | 2.3 | 88% |
|   | 2 | 2.8 | 1.8 | 93% |
|   | 0.4 | 3.0 | 1.4 | 0% |
| 8 | 50 | 5.4 | 1.8 | 100% |
|   | 10 | 3.3 | 1.4 | 60% |
|   | 2 | 3.2 | 2.6 | 33% |

(2) Determination of Acute Toxicity

The lethal dose, LD$_{50}$, of the compounds of Examples 1–8 was evaluated in mice after oral administration. The results obtained were as follows:

TABLE 3

| Product of Example | LD$_{50}$ (mg/kg) |
|---|---|
| 1 | ≅500 |
| 2 | ≅200 |
| 3 | ≅300 |
| 4 | ≅500 |
| 5 | ≅500 |
| 6 | ≅600 |
| 7 | ≅300 |
| 8 | ≅400 |

The above examples are illustrative of the invention, but are not to be deemed limitative. It is obvious to one skilled in the art that equivalent techniques and modifications may be employed without departing from the spirit of the invention and the scope of the appended claims.

What is claimed is:

1. A method of treating a patient suffering from a disease or ailment accompanied by gastric and gastroduodenal lesions comprising administering to said patient a gastric acid secretion inhibiting and cytoprotecting effective amount of a compound selected from the group consisting of a substituted derivative of 4-phenyl-4-oxo-2-butenoic acid of the formula (I)

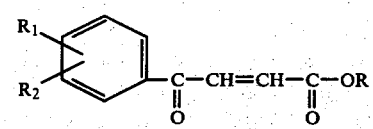

in which R represents hydrogen or alkyl containing 1 to 5 carbon atoms and R$_1$ and R$_2$, identical or different, both represent alkoxy containing 1 to 3 carbon atoms, or both represent halogen, or R$_1$ represents hydrogen and R$_2$ represents halogen, nitro or trifluoromethyl, or R$_1$ and R$_2$, located on adjacent carbon atoms, form a methylenedioxy group, and pharmaceutically acceptable salts.

2. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein R is as defined in claim 1, and R$_1$ and R$_2$ identical or different, both represent alkoxy containing 1 to 3 carbon atoms, or both represent halogen, or R$_1$ represents hydrogen and R$_2$ represents fluoro, 2-nitro or trifluoromethyl or R$_1$ and R$_2$ located on adjacent carbon atoms, form a methylenedioxy group, and pharmaceutically acceptable salts.

3. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein R is as defined in claim 1, and R$_1$ and R$_2$ identical or different, both represent alkoxy containing 1 to 3 carbon atoms, or both represent halogen, or R$_1$ represents hydrogen and R$_2$ represents halogen, nitro or a trifluoromethyl group.

4. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3 wherein $R_1$ and $R_2$, identical or different, both represent alkoxy containing 1 to 3 carbon atoms, or both represent halogen, or $R_1$ represents hydrogen and $R_2$ represents trifluoromethyl or fluoride.

5. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3 wherein $R_1$ and $R_2$, identical or different, both represent alkoxy containing 1 to 3 carbon atoms, or both represent halogen, or $R_1$ represents hydrogen and $R_2$ represents trifluoromethyl.

6. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3, wherein $R_1$ and $R_2$, identical or different, both represent alkoxy containing 1 to 3 carbon atoms.

7. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3 wherein $R_1$ and $R_2$ each represent a methoxy group and are situated in position 3 and 4.

8. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3 wherein $R_1$ and $R_2$, identical or different, both represent halogen.

9. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3, wherein $R_1$ represents hydrogen and $R_2$ a trifluoromethyl group.

10. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3, wherein the compound of formula (I) is (E)4-(3,4-dimethoxyphenyl)-4-oxo-2-butenoic acid or its pharmaceutically acceptable alkali metal, alkaline earth metal, and amine salts.

11. A method of treating a patient suffering from a disease or ailment accompanied by gastric and gastroduodenal lesions comprising administering to said patient a gastric acid secretion inhibiting and cytoprotecting effective amount of a compound as defined in claims 2 or 3, wherein the compound of formula (I) is (E)4-(4-trifluoromethylphenyl)-4-oxo-2-butenoic acid or is pharmaceutically acceptable alkali metal, alkaline earth metal, and amine salts.

12. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein $R_1$ and $R_2$, located at adjacent carbon atoms, together form a methylenedioxy group.

13. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein the compound of formula (I) is (E)4-(3,4-methylenedioxyphenyl)-4-oxo-2-butenoic acid or its pharmaceutically acceptable alkali metal, alkaline earth metal, and amine salts.

14. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein $R_1$ represents hydrogen and $R_2$ halogen.

15. A method of treating a patient suffering from a disease or ailment accompanied by gastric and gastroduodenal lesions comprising administering to said patient a gastric acid secretion inhibiting and cytoprotecting effective amount of a compound as defined in claim 1, wherein the compound of formula (I) is (E)4-(4-fluorophenyl)-4-oxo-2-butenoic acid or its pharmaceutically acceptable alkali metal, alkaline earth metal, and amine salts.

16. The method according to claims 1, 2, 3, 4, 5, 6, 7, 8, 9, 10, 11, 12, 13, 14 or 15, wherein the patient treated is suffering from hyperchlorhydria.

17. The method according to claims 1, 2, 3, 4, 5, 6, 7, 8, 9, 10, 11, 12, 13, 14 or 15, wherein the patient treated is suffering from gastric or gastroduodenal ulcer.

18. The method according to claims 1, 2, 3, 4, 5, 6, 7, 8, 9, 10, 11, 12, 13, 14 or 15, wherein the patient treated is suffering from gastritis.

19. The method according to claims 1, 2, 3, 4, 5, 6, 7, 8, 9, 10, 11, 12, 13, 14 or 15, wherein the patient treated is suffering from hiatal hernia.

20. The method according to claims 1, 2, 3, 4, 5, 6, 7, 8, 9, 10, 11, 12, 13, 14 or 15, wherein the patient treated is suffering from gastric and gastroduodenal disease accompanied by gastric hyperacidity.

* * * * *